US011684249B2

(12) United States Patent
Robertson

(10) Patent No.: US 11,684,249 B2
(45) Date of Patent: *Jun. 27, 2023

(54) IMAGING SYSTEM FOR ENDOSCOPE

(71) Applicant: Boston Scientific Scimed, Inc., Maple Grove, MN (US)

(72) Inventor: David W. Robertson, Framingham, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/782,664

(22) Filed: Feb. 5, 2020

(65) Prior Publication Data

US 2020/0170491 A1    Jun. 4, 2020

Related U.S. Application Data

(63) Continuation of application No. 15/710,609, filed on Sep. 20, 2017, now Pat. No. 10,588,499, which is a
(Continued)

(51) Int. Cl.
*A61B 1/06* (2006.01)
*A61B 1/07* (2006.01)
*G02B 23/24* (2006.01)

(52) U.S. Cl.
CPC .............. *A61B 1/0638* (2013.01); *A61B 1/07* (2013.01); *G02B 23/2469* (2013.01)

(58) Field of Classification Search
CPC ...... A61B 1/0638; A61B 1/07; G02B 23/2469
See application file for complete search history.

(56) References Cited

U.S. PATENT DOCUMENTS

| 3,971,065 A | 7/1976 | Bayer |
| 4,742,388 A | 5/1988 | Cooper et al. |

(Continued)

OTHER PUBLICATIONS

International Search Report for International Patent Application No. PCT/US2012/045397 dated Oct. 19, 2012, 3 pages.
(Continued)

*Primary Examiner* — Timothy J Neal
*Assistant Examiner* — William B Chou
(74) *Attorney, Agent, or Firm* — Bookoff McAndrews, PLLC

(57) ABSTRACT

Embodiments of the invention include an apparatus including at least one illumination source configured to emit illumination energy and an illumination control system to receive the illumination energy. The illumination control system is configured to control the illumination energy to output a sequence of different illumination wavelengths using the illumination energy. The apparatus also includes a plurality of optical fibers connected to the illumination control system and configured to sequentially output the different illumination wavelengths. Each optical fiber is configured to transmit a different illumination wavelength of the sequence to output the sequence of different illumination wavelengths from the optical fibers toward an object. The apparatus further includes an image capture device including a plurality of pixels, and each pixel of the image capture device is configured to detect the illumination energy associated with each of the plurality of different illumination wavelengths reflected from the object.

14 Claims, 4 Drawing Sheets

Related U.S. Application Data continuation of application No. 13/539,975, filed on Jul. 2, 2012, now Pat. No. 9,795,285.

(60) Provisional application No. 61/505,442, filed on Jul. 7, 2011.

(56) References Cited

U.S. PATENT DOCUMENTS

| | | | |
|---|---|---|---|
| 4,878,112 A | 10/1989 | Ieoka | |
| 4,945,366 A * | 7/1990 | Hisamichi | A61B 1/0655 396/17 |
| 5,233,416 A | 8/1993 | Inoue | |
| 5,523,786 A * | 6/1996 | Parulski | H04N 9/0451 348/E5.037 |
| 5,587,736 A * | 12/1996 | Walls | A61B 1/042 348/65 |
| 6,363,088 B1 | 3/2002 | Alphonse et al. | |
| 6,485,414 B1 | 11/2002 | Neuberger | |
| RE39,977 E * | 1/2008 | Treado | G01J 3/2823 250/339.02 |
| 7,713,192 B2 | 5/2010 | Murata | |
| 2002/0014595 A1 | 2/2002 | Sendai et al. | |
| 2002/0062061 A1 | 5/2002 | Kaneko et al. | |
| 2002/0105505 A1 * | 8/2002 | Sendai | A61B 5/0086 345/204 |
| 2003/0038944 A1 * | 2/2003 | Hamalainen | G01J 5/60 356/432 |
| 2004/0186351 A1 * | 9/2004 | Imaizumi | A61B 5/0071 600/160 |
| 2005/0215911 A1 * | 9/2005 | Alfano | A61B 1/041 600/476 |
| 2006/0211915 A1 | 9/2006 | Takeuchi et al. | |
| 2007/0019156 A1 * | 1/2007 | Fink | A61B 3/16 351/200 |
| 2007/0182962 A1 * | 8/2007 | Bearman | G01J 3/18 356/328 |
| 2008/0027286 A1 * | 1/2008 | Xie | A61B 5/0084 600/181 |
| 2008/0195128 A1 * | 8/2008 | Orbay | A61B 17/3421 600/183 |
| 2009/0012361 A1 | 1/2009 | Mackinnon et al. | |
| 2009/0149706 A1 | 6/2009 | Yamazaki et al. | |
| 2009/0180115 A1 * | 7/2009 | Wilson | G01J 3/1838 356/328 |
| 2010/0134608 A1 | 6/2010 | Shibasaki | |
| 2010/0134802 A1 * | 6/2010 | Chan | G01N 21/4795 356/497 |
| 2011/0063427 A1 * | 3/2011 | Fengler | H04N 5/332 348/E5.09 |
| 2011/0069315 A1 * | 3/2011 | He | G01J 3/28 356/425 |
| 2011/0199500 A1 | 8/2011 | Shimizu et al. | |
| 2011/0206291 A1 * | 8/2011 | Kashani | G01J 4/04 356/73 |
| 2011/0275912 A1 * | 11/2011 | Boyden | A61L 31/026 600/309 |
| 2012/0071765 A1 | 3/2012 | Chinnock | |
| 2012/0123205 A1 * | 5/2012 | Nie | A61B 5/0084 600/109 |
| 2012/0209090 A1 * | 8/2012 | Goodall | A61B 5/14503 604/523 |
| 2015/0177071 A1 * | 6/2015 | Meimoun | G01J 9/00 250/229 |
| 2019/0162977 A1 | 5/2019 | Koyama et al. | |

OTHER PUBLICATIONS

CRi Instruments, "High-Resolution Color From Your Monochrome Camera," reprinted from http://web.archive.org/web/20070819025049/http://www.cri-inc.com/files/MicroColorBrochure.pdf, available Aug. 19, 2007 (4 pages).

Olympus, "Digital Colour Imaging in Fluorescence Microscopy," reprinted from http://web.archive.org/web/20090315021952//http:/lwww.microscopy.olyumpus.eu/microscopes/39 9278.htm, available Mar. 15, 2009, printed on Jun. 29, 2012 (4 pages).

El Gamal, A., et al., "CMOS Image Sensors," IEEE Circuits & Devices Magazine, pp. 6-20, May/Jun. 2005.

Guttosch, R.J., "Investigation of Color Aliasing of High Spatial Frequencies and Edges for Bayer-Pattern Sensors and Foveon X3® Direct Image Sensors," 2005 (8 pages).

* cited by examiner

IMAGING SYSTEM FOR ENDOSCOPE

PRIORITY

This application is a Continuation of U.S. patent application Ser. No. 15/710,609, filed Sep. 20, 2017, which is a Continuation of U.S. patent application Ser. No. 13/539,975, filed Jul. 2, 2012, now U.S. Pat. No. 9,795,285, which claims the benefit of priority from U.S. Provisional Application No. 61/505,442, filed Jul. 7, 2011, each of which is incorporated herein by reference in its entirety.

FIELD

Embodiments of the invention include imaging systems and more particularly imaging systems for endoscopes and related methods of use.

BACKGROUND

Conventional digital imaging systems may include an illumination source and an image capture device including a plurality of pixels configured to detect light intensity. The conventional imaging system may also include one or more filters deposited in a predetermined pattern, such as in a Bayer pattern, on top of the pixels. In the Bayer pattern, blue, red, and green color filters are arranged over a set of pixels so that, for every set of four pixels, two of the pixels is covered with a green filter, one pixel is covered with a blue filter, and one pixel is covered with a red filter. As a result, light to each pixel is filtered so that each pixel only records light intensity information for the specific color (i.e., red, green, or blue) deposited on the respective pixel. A processor may be used to process the color values for each pixel to form a full-color composite image. Since each pixel is capable of detecting light intensity information for only one specific color, the conventional digital imaging system is inefficient, especially for miniaturized cameras with a limited number of pixels. For example, only about a quarter of the pixels may be used to detect red or blue illumination, and interpolation may be used to provide red or blue information between those pixels. Accordingly, a need exists for a smaller, more efficient imaging system.

SUMMARY

In accordance with an embodiment, an apparatus includes at least one illumination source configured to emit illumination energy and an illumination control system connected to the at least one illumination source to receive the illumination energy. The illumination control system is configured to control the illumination energy to output a sequence of different illumination wavelengths using the illumination energy. The apparatus also includes an elongate member configured to be at least partially inserted into a patient, and a plurality of optical fibers connected to the illumination control system and disposed within the elongate member. The plurality of optical fibers are configured to sequentially output the different illumination wavelengths, and each optical fiber is configured to transmit a different illumination wavelength of the sequence to output the sequence of different illumination wavelengths from the optical fibers toward an object. The apparatus further includes an image capture device including a plurality of pixels, and each pixel of the image capture device is configured to detect the illumination energy associated with each of the plurality of different illumination wavelengths reflected from the object. The image capture device is configured to produce a plurality of image frames, and each of the image frames is associated with one of the illumination wavelengths.

In accordance with another embodiment, a method includes positioning a distal end of an elongate member near an object, producing illumination energy associated with different illumination wavelengths to output a sequence of the different illumination wavelengths, and transmitting the illumination energy through a plurality of optical fibers extending through the elongate member. Each optical fiber is configured to transmit a different illumination wavelength of the sequence to output the sequence of different illumination wavelengths towards the object. The method also includes illuminating the object using the illumination energy transmitted through the plurality of optical fibers, and using each of a plurality of pixels of an image capture device located in the elongate member to detect the illumination energy reflected from the object associated with each of the illumination wavelengths. The method further includes producing a plurality of image frames based on the detected illumination energy, each image frame being associated with one of the illumination wavelengths.

In accordance with a further embodiment, an endoscopic system includes an elongate member configured to be at least partially inserted into a patient, a plurality of optical fibers extending through the elongate member, and at least one illumination source coupled to the plurality of optical fibers and configured to direct illumination energy associated with a plurality of different illumination wavelengths through the plurality of optical fibers such that the different illumination wavelengths of the illumination energy are produced in a sequence. Each optical fiber is configured to transmit a different illumination wavelength of the sequence to output the sequence of different illumination wavelengths. The endoscopic system also includes an image capture device disposed in the elongate member, and the image capture device includes a plurality of pixels. Each pixel is configured to detect the illumination energy associated with each of the plurality of different illumination wavelengths. The image capture device is configured to produce a plurality of image frames, and each of the image frames is associated with one of the illumination wavelengths. The endoscopic system further includes a processor coupled to the image capture device and configured to receive the plurality of image frames from the image capture device and to produce a composite image based on at least two of the image frames.

Additional objects and advantages of the invention will be set forth in part in the description which follows, and in part will be obvious from the description, or may be learned by practice of the invention. The objects and advantages of the invention will be realized and attained by means of the elements and combinations particularly pointed out below.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to exemplary embodiments of the invention, examples of which are illustrated in the accompanying drawings. Wherever possible, the same reference numbers will be used throughout the drawings to refer to the same or like parts.

The terms "proximal" and "distal" are used herein to refer to the relative positions of the components of an exemplary endoscopy system 10. When used herein, "proximal" refers to a position relatively closer to the exterior of the body, or closer to the surgeon or other user using the endoscopy system 10. In contrast, "distal" refers to a position relatively further away from the surgeon or other user using the endoscopy system 10, or closer to the interior of the body.

Figure 1:
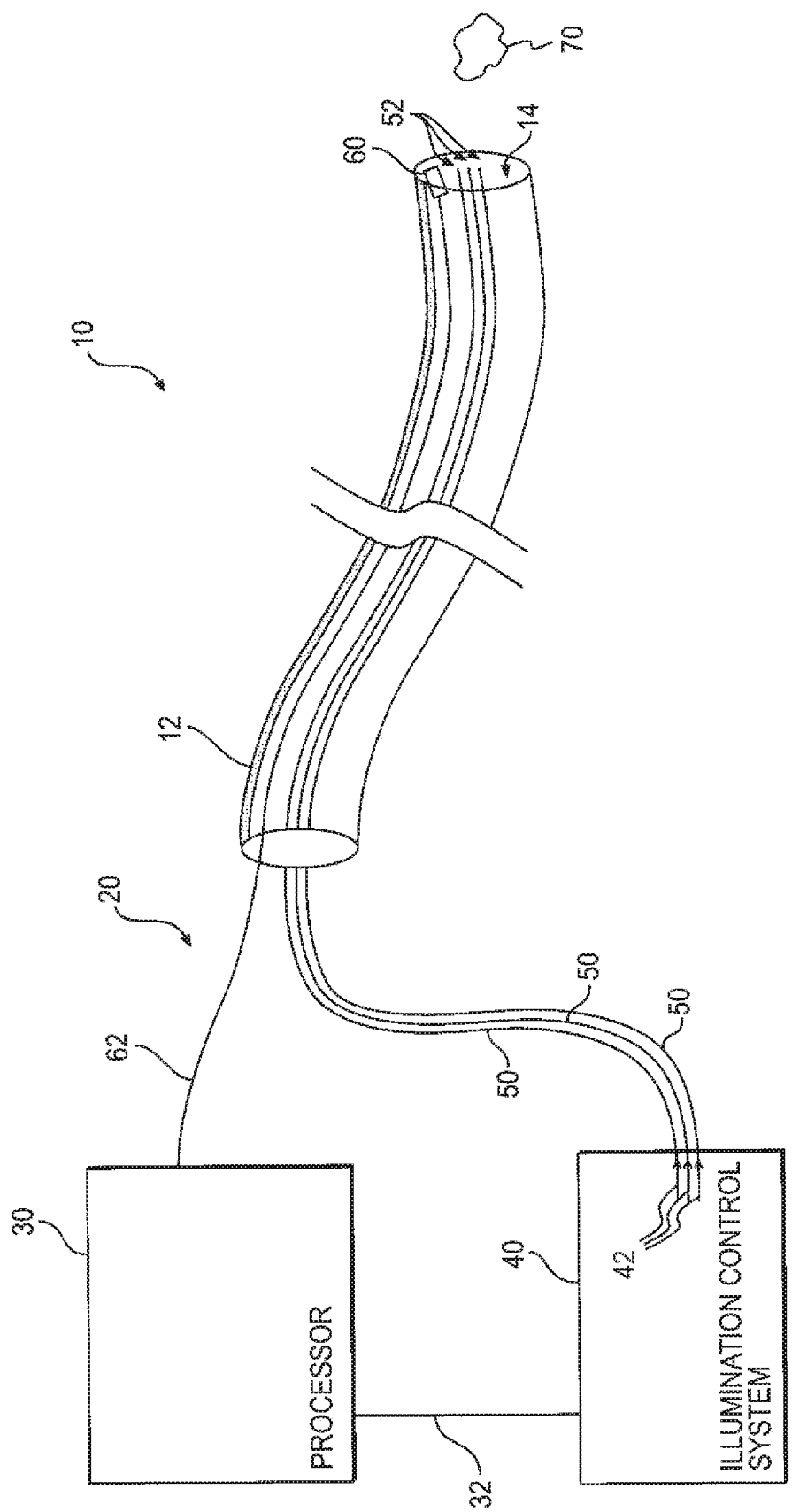
FIG. 1 is a schematic view of an endoscopy system including an imaging system, according to an exemplary embodiment.

FIG. 1 shows the endoscopy system 10 that may be used for any therapeutic or diagnostic endoscopic procedure, according to an exemplary embodiment. The phrase "endoscopic procedure" is broadly used to indicate any medical procedure that may be performed by inserting an endoscope, guide tube, catheter, or any other medical device into the body through any anatomic opening. The endoscopy system 10 includes an elongate member 12 and an imaging system 20 including a processor 30 and an illumination control system 40.

The elongate member 12 may be included in an endoscope, guide tube, catheter, or any other medical device, and may include one or more lumens 14 through which one or more working instruments may be inserted. The elongate member 12 may be capable of being used for the purpose of performing an endoscopic procedure. At least the distal end of the elongate member 12 may be advanced into the patient, e.g., through a gastrointestinal (GI) tract, urinary tract, or other body lumen, channel, or cavity accessed during a medical procedure (e.g., a procedure relating to urology, gynecology, cardiology, pulmonary, biliary, nasal, etc., such as procedures relating to kidney stones or biliary stones). The elongate member 12 and the working instruments inserted through the lumen(s) 14 of the elongate member 12 may be made of any suitable material, e.g., a suitable biocompatible material capable of being advanced through the patient, and may be flexible, e.g., to be able to traverse tortuous anatomy.

One of the working instruments that may be inserted through the lumen(s) 14 of the elongate member 12 may include one or more optical fibers 50 having one or more respective distal ends 52. For example, in the exemplary embodiment, three optical fibers 50 are provided as will be described below. It is to be understood, however, that fewer than three or more than three optical fibers 50 may be provided. The optical fibers 50 may be inserted through the lumen 14 of the elongate member 12 or may be integrated into the elongate member 12, e.g., extending to the distal end or a distal face of the elongate member 12. Accordingly, the optical fibers 50 and/or the elongate member 12 may be moved longitudinally (e.g., along the distal direction), laterally, and/or rotationally, so that the distal ends 52 of the optical fibers 50 are positioned as desired near a location inside the patient to be imaged (the imaging location). The imaging location, for example, may be a location where an endoscopic procedure is performed.

The proximal ends of the optical fibers 50 may be coupled to the illumination control system 40 so that illumination energy 42 produced by the illumination control system 40 may be transferred from the illumination control system 40, through the lengths of the respective optical fibers 50, and out through the distal ends 52 of the optical fibers 50 toward the imaging location inside the patient. The optical fibers 50 may be steerable by the user of the endoscopy system 10 as described above to direct the illumination energy 42 from the distal ends 52 of the optical fibers 50 toward the imaging location at a desired angle and position with respect to the imaging location.

In an exemplary embodiment, the illumination control system 40 may include multiple illumination sources as will be described below. The illumination sources may be any type of source configured to emit the illumination energy 42, e.g., a beam of light capable of having one of a plurality of illumination wavelengths that are detectable by an image capture device 60, and the illumination energy 42 may be directed from the distal ends 52 of the optical fibers 50 towards an object 70.

Figure 2:
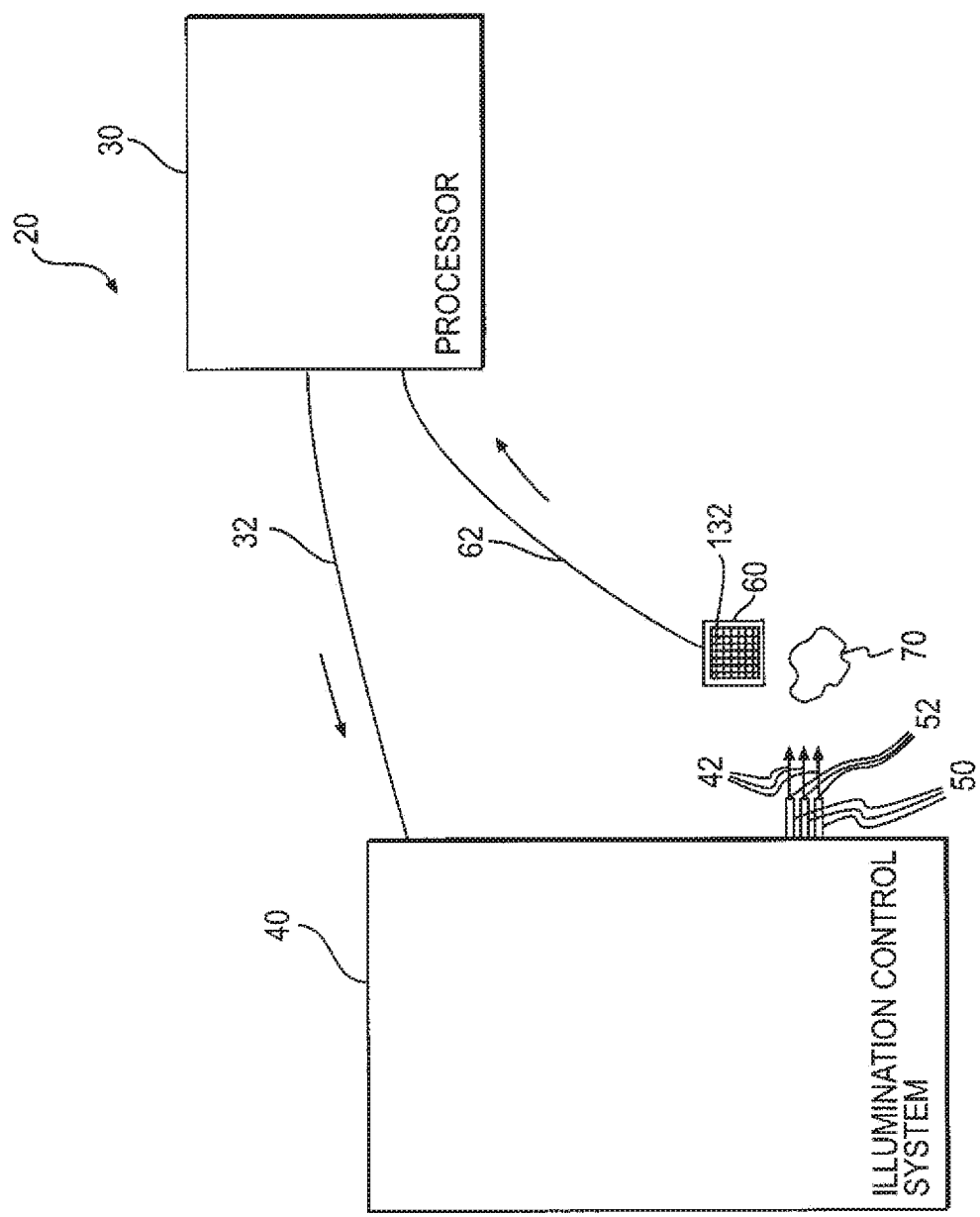
FIG. 2 is a schematic view of the imaging system of FIG. 1.

The working instruments may also include an instrument including an image capture device 60. For example, the image capture device 60 may be a charge coupled device (CCD), complementary metal oxide semiconductor (CMOS), or other image capture device including one or more pixels 132, as shown in FIG. 2. The image capture device 60 may be inserted through the lumen 14 of the elongate member 12 (or a different lumen than the one through which the optical fibers 50 are inserted) or may be integrated into the elongate member 12, e.g., near the distal end or on a distal face of the elongate member 12. Accordingly, the image capture device 60 and/or the elongate member 12 may be moved longitudinally, laterally, and/or rotationally, so that the image capture device 60 is positioned as desired near the imaging location inside the patient. Alternatively, the image capture device 60 may be located near a proximal end of the elongate member 12 or at another location in the elongate member 12. In such an embodiment, the image capture device 60 may be connected to fiber optics or other communication lines extending to the distal end or the distal face of the elongate member 12. The fiber optics may receive illumination energy through an end disposed near the distal end or distal face of the elongate member 12 and may transmit the received illumination energy to the image capture device 60.

Referring to FIG. 2, the working instrument including the image capture device 60 may also include a unidirectional or bidirectional connecting line 62, such as a conductor or fiber optics that couples the image capture device 60 to the processor 30. Alternatively, the image capture device 60 may communicate with the processor 30 wirelessly. The connecting line 62 may transfer information (e.g., image frames) or other signals from the image capture device 60 to the processor 30 as described below. Also, the connecting line 62 may transfer control information or other signals from the processor 30 to the image capture device 60.

A unidirectional or bidirectional connecting line 32 may couple the illumination control system 40 to the processor 30. For example, the connecting line 32 may transfer information or other signals from the processor 30 to the illumination control system 40, such as information for controlling the illumination control system 40, e.g., duration, intensity, wavelength, timing, etc., of the illumination energy 42. Also, the connecting line 32 may transfer information or other signals from the illumination control system 40 to the processor 30, such as information relating to the operation of the illumination control system 40, e.g., status signals to the processor 30 associated with emission status (e.g., timing of emissions of the illumination energy 42, the wavelengths of the emitted illumination energy 42, etc.). In an embodiment, the illumination control system 40 and the processor 30 may be provided in a common housing or other structure (e.g., a handle of the endoscopic system 10) that is not inserted into the patient.

The image capture device 60 may be any type of image capture device 60 configured to sense or detect the illumination energy reflected off the object 70 and produce information based on the sensed illumination energy. For example, the image capture device 60 may produce an image frame that includes information associated with the detected illumination energy. The image frame may include intensity values detected by one or more pixels 132 of the image capture device 60. For example, when red illumination is produced by the illumination control system 40, each pixel 132 of the image capture device 60 may produce information or a value corresponding to the intensity of the red illumination detected by the respective pixels 132. The value may have a digital or analog representation, e.g., a number, a letter, a voltage, a current, etc. The image frames may also include other information, e.g., information associated with the ordering or location of the pixels, timing of the image frames, etc.

The operation of the imaging system 20, according to an exemplary embodiment, will now be explained. When a power source (not shown) is applied to the image capture device 60, the image capture device 60 may produce image frames at periodic intervals and may transmit the image frames to the processor 30 (e.g., automatically and without any triggering or other control from the processor 30).

The processor 30 may receive and process the image frames to determine the timing of the image frames. After determining the timing of the image frames, the processor 30 may signal the illumination control system 40 to produce a sequence, e.g., a sequence of red, green, and blue illumination, at specific times and durations that are synchronized to the image frames produced by the image capture device 60. Thus, the illumination control system 40 may produce a repeating sequence of red, green, and blue illumination, e.g., associated with the sequence of image frames produced by the image capture device 60. Since the image frames may include information representing the intensity of the illumination energy detected by the pixels 132 of the image capture device 60, synchronization is used so that the processor 30 may keep track of the color of illumination supplied by the illumination control system 40 when each image frame is produced by the image capture device 60. Having synchronized the illumination control system 40 to the image capture device 60, the processor 30 may receive the image frames from the image capture device 60 and may combine one or more sequence of image frames, e.g., one image frame associated with red illumination, one image frame associated with green illumination, and one image frame associated with blue illumination, to produce a full-color composite image frame. The full-color image frame may be displayed in real-time to the user using a video monitor or other display device connected to the processor 30, and/or may be stored on media coupled to the processor 30 for later viewing.

Alternatively, instead of producing a sequence of red, green, and blue illumination, the processor 30 may signal the illumination control system 40 to produce a sequence of illumination energy of other different wavelengths. Then, the processor 30 may determine the desired time and wavelengths with which the illumination control system 40 should emit the illumination energy 42. Then, the processor 30 may transmit control signals to the illumination control system 40 so that the illumination control system 40 may emit the illumination energy 42 at the desired time and wavelengths. The illumination control system 40 may sequentially emit the illumination energy 42 at the plurality of different wavelengths toward the object 70 located at the imaging location in synchronization with the production of image frames by the image capture device 60.

Although image frames are discussed herein as being associated with a single wavelength or color, the image frames may generally be associated predominantly with the single wavelength or color, and/or may generally be associated with a band of wavelengths, e.g., centered about a particular wavelength or band of wavelengths. Furthermore, the bands of wavelengths may overlap or be discontinuous. For example, the illumination control system 40 may sequentially emit the illumination energy 42 at three bands of wavelengths of light, e.g., bands centered at 650 nm (associated with red light), 510 nm (associated with green light), and 475 nm (associated with blue light), each for a period of time associated with the image capture device 60 for producing an image frame for each respective illumination wavelength band. Thus, the image frames produced by the image capture device 60 may be associated with a sequence of predominantly red, green, and blue illumination energy. Alternatively, different sequences and/or wavelength bands of illumination energy may be emitted by the illumination control system 40 to illuminate the object 70.

The processor 30 may provide a single control signal to the illumination control system 40 to begin a predetermined sequence of emissions of the illumination energy 42 at the different wavelengths to synchronize emission of the illumination energy 42 to the image frames. Alternatively, the processor 30 may periodically send control signals to the illumination control system 40 to synchronize emission of the illumination energy 42 to the image frames. As another alternative, emission of the illumination energy 42 may be synchronized to the image frames using other methods, e.g., by transmitting a startup signal to the processor 30 to indicate that image frames begin at a predetermined time and/or interval. As another alternative, the processor 30 may monitor a signal from the power supply to the image capture device 60 to determine when the image capture device 60 begins to produce signals associated with the image frames, e.g., based on a voltage, current, or other power supply characteristic and a known startup or initialization time.

The processor 30 may also use information received from the illumination control system 40 to synchronize the emission of the illumination energy 42 from the illumination control system 40 with signals received from the image capture device 60. When the emission of the illumination energy 42 is synchronized with the signals received from the image capture device 60 relating to the timing of the image frames, the processor 30 may use information received from the illumination control system 40 to determine which particular wavelength produced by the illumination control system 40 is associated with a particular image frame produced by the image capture device 60.

The processor 30 may interpret each image frame received from the image capture device 60. The processor 30 may combine a sequence of image frames to produce the composite full-color image. For example, in an embodiment, the processor 30 may combine three image frames: a first image frame associated with illumination energy substantially centered at a wavelength of 650 nm (associated with red light), a second image frame associated with illumination energy substantially centered at a wavelength of 510 nm (associated with green light), and a third image frame associated with illumination energy substantially centered at a wavelength of 475 nm (associated with blue light) to produce a full-color image in red-green-blue (RGB) color space. In other embodiments, as described above, different sequences or wavelength bands of illumination energy may be emitted by the illumination control system 40 to illuminate the object 70. For example, some objects may be more effectively imaged under illumination having wavelength bands associated with various shades of a particular color other than under illumination at a sequence of RGB illumination wavelengths, including infrared or ultraviolet wavelength bands.

The processor 30 may be configured to adjust the intensity and/or duration of emissions of the illumination energy 42 emitted by the illumination control system 40. Adjustments of the intensity and/or duration of the emissions of the illumination energy 42 may result in a more true-color composite image in certain instances. Such adjustments may also be used, for example, to emphasize or soften certain features, control image brightness, control color balance, etc. For example, decreasing the intensity of illumination at a predominantly red wavelength band, in the case of a sequence of illumination at RGB illumination wavelengths, may result in a softening or partial removal of red components of the full-color image of the object 70. Similar adjustments may be used in sequences of illumination other than RGB to similarly emphasize or soften certain features of the object 70. Accordingly, the processor 30 may send control signals to the illumination control system 40 to adjust the illumination energy 42 associated with one or more of the wavelength bands sequentially emitted by the illumination control system 40. As a result, the imaging system 20 may provide real-time image feedback processing for controlling image brightness, color balance, etc.

The illumination control system 40 serves as a multiple-wavelength source and selector. As will be described below, the illumination control system 40 may be configured to emit illumination energy 42 at multiple different wavelength bands directed toward the object 70. The sequence of the different wavelength bands may be selectable and controlled.

Figure 3:
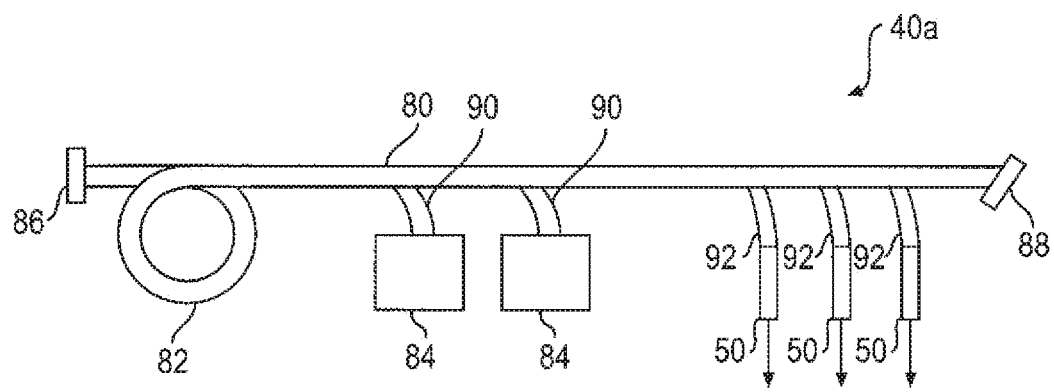
FIGS. 3-5 are schematic views of an illumination control system of the imaging system of FIGS. 1 and 2, according to various exemplary embodiments.
Figure 4:
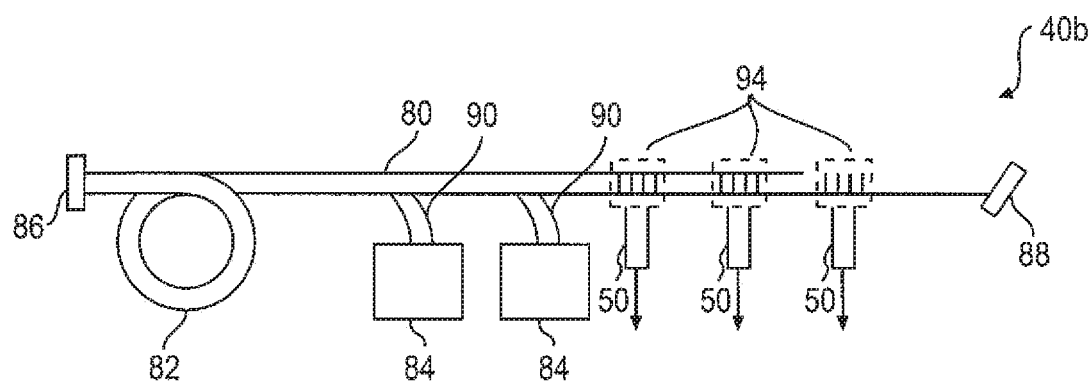
Figure 5:
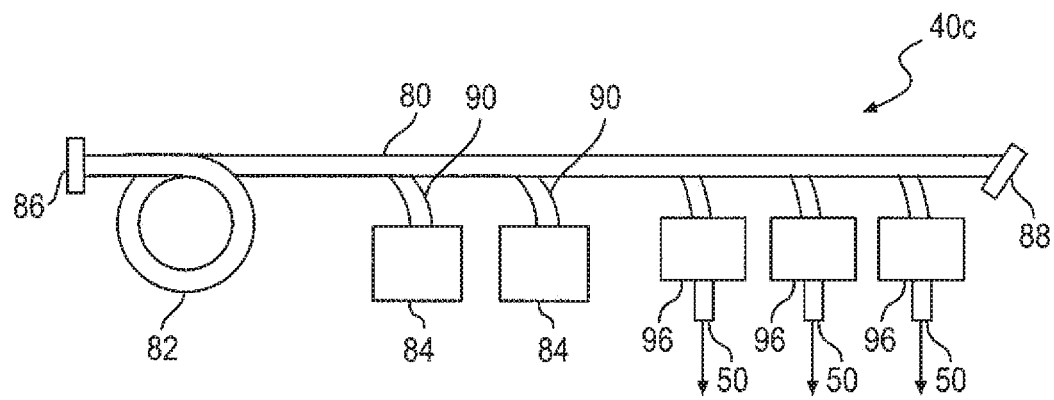

FIGS. 3-5 show various embodiments of the illumination control system 40. For example, FIG. 3 shows an illumination control system 40a including an optical fiber section 80, a coiled fiber portion 82, pump light sources 84, a reflector 86, a facet 88, and wavelength division multiplexers (WDMs) 90, 92.

The pump light sources 84 are sources of energy, e.g., sources of energy configured to operate at one frequency or wavelength band for generating energy at another frequency or wavelength band. The pump light sources 84 are coupled to the optical fiber section 80 by the WDMs 90, and the optical fiber section 80 may be pumped with illumination energy at one frequency or wavelength band from each respective pump light source 84 via the respective WDMs 90. Accordingly, the pump light sources 84 may serve as an illumination sources.

The WDMs 90, 92 are wavelength-sensitive devices that may be used to couple power at a specific wavelength band (or frequency band) to a fiber. For example, the WDMs 90 may couple a pump light source supplying stimulation energy to the optical fiber section 80, and the WDMs 92 may selectively transmit illumination energy out of the optical fiber section 80. The WDMs 90, 92 may be made by fusing fibers together so that illumination energy propagating in one fiber core may be transmitted to one or more other optical fiber cores, e.g., one or more of the optical fibers 50, etc., through the WDMs 92. The WDMs 90, 92 may be configured to transmit substantially all illumination energy from one fiber to another over a specified bandwidth, e.g., by adjusting the interaction length and the spacing between the fiber cores.

The optical fiber section 80 and the coiled fiber portion 82 may, for example, be configured to form a broadband laser and may guide the illumination energy along its fiber core. The reflector 86 may be formed, for example, by cleaving a first facet of the optical fiber section 80 perpendicular to the fiber core and forming a mirrored surface. The second facet 88 of the fiber section may be, for example, ground and polished at an angle. In this manner, illumination energy generated and propagated in the fiber core of the optical fiber section 80 may be transmitted to the WDMs 92, which transmit light of a selected wavelength band out of the optical fiber section 80. The three WDMs 92 may be used to separate the broad band light into, e.g., red, green, and blue components, respectively. Thus, the illumination control system 40a may generate light at various frequency bands by selecting, e.g., red, green, and blue components (or other components of different wavelength bands) from broad band (i.e., white) light.

FIG. 4 shows an illumination control system 40b including three diffraction gratings 94 for separating the broad band light into, e.g., red, green, and blue components, respectively, instead of the three WDMs 92. FIG. 5 shows a illumination control system 40c including three adjustable color filters 96 for separating the broad band light into, e.g., red, green, and blue components, respectively, instead of the three WDMs 92. The adjustable color filters 96 may be any optical devices that may be adjusted using an adjustment mechanism to transmit illumination energy at different wavelengths, e.g., color wheels, voltage- or current-dependent dielectric devices, fiber optic band pass filters, and/or acousto-optical devices. Although the illumination control systems 40a-40c are shown using contra-directional pumping, co-directional pumping may also be used. Certain components of the illumination control systems 40a-40c are disclosed in further detail, for example, in U.S. Pat. No. 6,363,088 entitled "All Solid-State Power Broadband Visible Light Source," which is hereby incorporated by reference in its entirety.

Thus, the illumination control systems 40a-40c may generate illumination energy at particular wavelengths or bands of wavelengths by separating broadband (i.e., white) light into single or predominantly single wavelengths using the WDMs 92, the diffraction gratings 94, or the adjustable color filters 96, respectively. For example, the WDMs 92, the diffraction gratings 94, and/or the adjustable color filters 96 may be used to select illumination energy predominantly at wavelengths associated with, e.g., infrared, red, green, blue, and ultraviolet light from broad band light.

Illumination energy output from the WDMs 92 (or the diffraction gratings 94, the adjustable color filters 96, etc.) of the illumination control system 40a-40c (e.g., separated or filtered into three different wavelength bands) is then transmitted via the optical fibers 50 connected to the respective WDMs 92 and directed by the respective optical fibers 50 to the imaging location in the patient. For example, in an embodiment, one optical fiber 50 may transmit red illumination, another optical fiber 50 may transmit green illumination, and yet another optical fiber 50 may transmit blue illumination at specific times and durations that are synchronized to the image frames produced by the image capture device 60, as described above.

Figure 6:
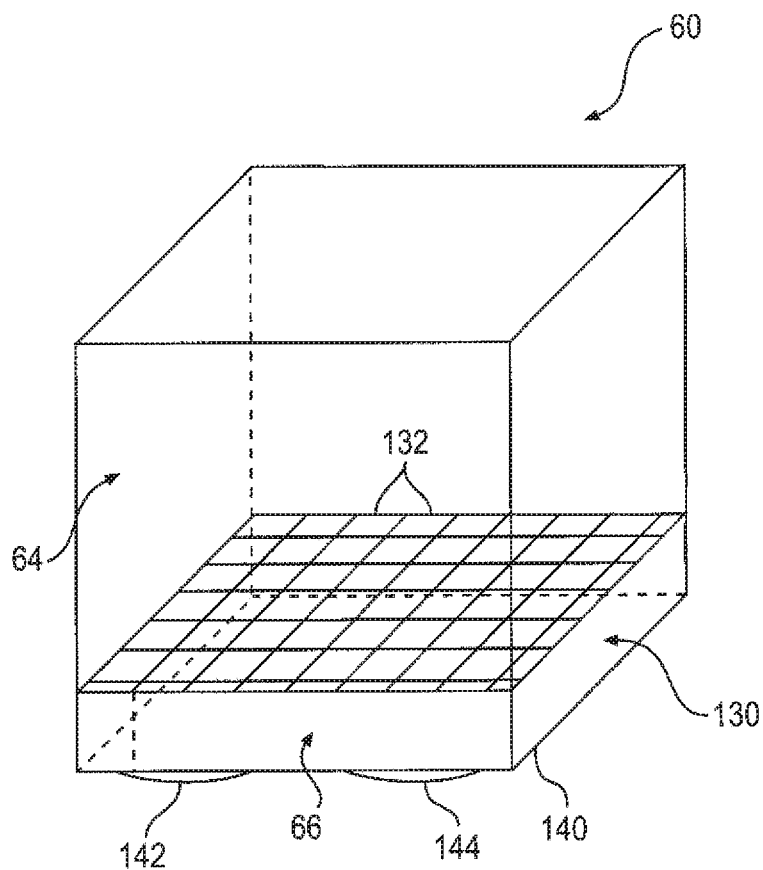
FIG. 6 is a perspective view of an image capture device of the imaging system of FIGS. 1 and 2.
Figure 7:
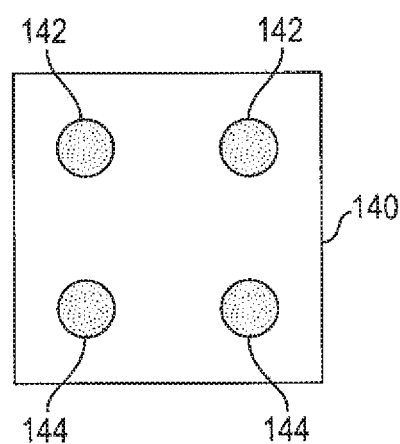
FIG. 7 is a distal end view of an image capture device of the imaging system of FIGS. 1 and 2.

FIGS. 6 and 7 show the image capture device 60 according to an exemplary embodiment. The image capture device 60 may include focusing optics 64, circuitry 66, and a pixel array 130 including the plurality of pixels 132, e.g., arranged in a row and/or column format.

In an exemplary embodiment, the image capture device 60 is not configured to separate the broad band light into the illumination energy at the different wavelengths. For example, no color or wavelength filters are deposited on or otherwise arranged over the pixel array 130 in the image capture device 60. The functions of separating the broad band light into illumination energy at the different wavelengths and selecting the single wavelength band may be performed external to the elongate member 12 and the patient (e.g., in the illumination control system 40) and without the image capture device 60 and the connecting line 62. These functions may also be performed without including filters or other structure in the image capture device 60 for separating the broad band light into the illumination energy at the different wavelengths, and without sending control signals to the image capture device 60.

Furthermore, each pixel 132 may be configured to detect illumination energy of any wavelength in the visible spectrum. For example, when an object is imaged serially with each of red, green, and blue illumination, the image capture device 60 may use each pixel 132 to produce an image frame of the object 70 based on each color of illumination. The image frames may then be combined to form a composite, full-color image in RGB color space. This method of forming a full-color image may advantageously avoid interpolation, avoid manufacturing processes to produce a pixel mask or filter, and avoid per-pixel wavelength-dependent lenses. These advantages may result in a smaller, less complex, and less expensive image capture device 60.

Furthermore, in video applications, the image capture device 60 may produce images at a rate sufficient to prevent visual flickering. In the example of a series of red, green, and blue illumination, a composite, full-color image in RGB color space may be produced based on three image frames, one image frame for each color (or wavelength band) within a given time period. Thus, in such embodiments, the image capture device 60 may produce image frames at a rate that is at least three times faster than the rate of the composite frame, which may be at a rate sufficient to prevent visual flickering. For example, the circuitry 66 may be implemented in the image capture device 60 so that a desired frame rate can be achieved.

The processor 30 may produce composite images, and may be external to the image capture device 60 and also external to the elongate member 12. This allows logic in the circuitry 66 to be minimized to simplify, reduce the size of, and lower the cost of the image capture device 60. Certain processing functions may be accomplished by the on-chip circuitry 66 of the image capture device 60, such as, for example, internal timing, image acquisition sequencing, signal output sequencing, and output signal formatting. Such minimal image capture devices 60 may be particularly useful in space-constrained and disposable applications by shifting relatively complex processing functions to another device (e.g., the processor 30). For example, the image capture device 60 may be disposed in a disposable component (e.g., a disposable working instrument) and may be operatively coupled to a more complex, larger, reusable apparatus (e.g., the elongate member 12 of an endoscope, catheter, etc.).

As shown in FIG. 7, a proximal surface 140 of the image capture device 60 may include a plurality of connection pads 142, 144 for connecting the image capture device 60 to the processor 30 and/or other devices. For example, two connection pads 142 may be provided to connect the image capture device 60 to a power source (e.g., directly or via the processor 30), and two connection pads 144 may provide the image capture device 60 with a signal output to the processor 30. The image capture device 60 may be configured to use various methods of signaling via the connection pads 144. For example, the image capture device 60 may use separate ground and signal lines or other arrangements for transmitting signals associated with image frame data to an external device, such as the processor 30. Furthermore, the image capture device 60 may be configured to use various encoding protocols for transmitting image frame data. In one embodiment, the image capture device 60 may encode data values in pulse duration. In other embodiments, the image capture device 60 may encode data in return-to-zero pulses or non-return-to-zero pulses.

Alternatively, the connection pads 142, 144 may be provided on one or more surfaces of the image capture device 60 other than, or in addition to, the proximal surface 140. For example, the connection pads 142, 144 may be placed on a side surface of the image capture device 60 to avoid bending the wires or other elements connecting to the connection pads 142, 144. As another alternative, the image capture device 60 may include more or less than four connection pads 142, 144.

The image capture device 60 may operate independent of external control signals, e.g., from the processor 30, the illumination control system 40, or other device. For example, when power, current, or voltage is applied to the image capture device 60, the image capture device 60 may produce the image frames at the output connection pads 144 without receiving any external control signals. In some embodiments, the image capture device 60 may produce startup signals to signal to an attached device (e.g., the processor 30) that the image capture device 60 is producing image frames. The absence of external control signals input to the image capture device 60 may simplify the design of the circuitry 66 because, for example, the circuitry 66 may not need to interpret incoming signals, or interrupt or restart its operation to process input signals.

Any aspect set forth in any embodiment may be used with any other embodiment set forth herein. Every device and apparatus set forth herein may be used in any suitable medical procedure, may be advanced through any suitable body lumen and body cavity, and may be used for imaging any suitable body portion.

It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus comprising:
   a handle;
   a member having a proximal end and a distal end, the proximal end connected to the handle and the distal end configured to be at least partially inserted into a patient;
   at least one illumination light source configured to emit different wavelengths of illumination energy;
   an illumination control system connected to the at least one illumination light source and housed in the handle, wherein the illumination control system is configured to control an output sequence for each of the different wavelengths of the illumination energy such that only one wavelength of the different wavelengths is output at a given time in the sequence;
   an image capture device including a plurality of pixels, wherein, based on the sequence, the image capture device is configured to form an image for each of the different wavelengths of the illumination energy emitted by the at least one illumination light source and detected by each of the plurality of pixels, and wherein each of the plurality of pixels is configured to detect illumination energy of each wavelength in the visible spectrum, including each of the different wavelengths, without the image capture device having a structure for separating broad band light into the illumination energy at the different wavelengths; and
   a processor housed in the handle and configured to generate a composite image from the image formed for each of the different wavelengths of the illumination energy based on the sequence.

2. The apparatus of claim 1, wherein, to detect the illumination energy, the plurality of pixels are configured to receive the illumination energy from an object onto which the illumination energy is emitted.

3. The apparatus of claim 2, wherein each of the plurality of pixels is configured to detect illumination energy of a same wavelength to form the image for each of the different wavelengths of the illumination energy.

4. The apparatus of claim 1, wherein the different wavelengths of the illumination energy include wavelengths corresponding to a green, a blue, and a red light.

5. The apparatus of claim 1, wherein the composite image is formed based on an intensity of the illumination energy of each of the different wavelengths.

6. The apparatus of claim 1, wherein each of the different wavelengths of the illumination energy emitted from the at least one illumination light source is a wavelength in the visible spectrum.

7. An apparatus comprising:
   a handle;
   a member having a proximal end and a distal end, the proximal end connected to the handle and the distal end configured to be at least partially inserted into a patient;
   at least one illumination light source configured to emit illumination energy of different wavelengths, including at least a first illumination energy of a first wavelength and a second illumination energy of a second wavelength different from the first wavelength;
   an illumination control system connected to the at least one illumination light source and housed in the handle, wherein the illumination control system is configured to control the illumination energy to output at least the first illumination energy and the second illumination energy in a sequence such that only one wavelength of the different wavelengths is output at a given time in the sequence;
   an image capture device including a plurality of pixels, wherein, based on the sequence, the image capture device is configured to form an image for each wavelength of illumination energy emitted by the at least one illumination light source and detected by each of the plurality of pixels, including at least the first illumination energy and the second illumination energy output sequentially, and wherein each of the plurality of pixels is configured to receive and detect illumination energy of each wavelength in the visible spectrum and only one wavelength in the visible spectrum at a given time such that the first wavelength is detected when the first illumination energy is received and the second wavelength is detected when the second illumination energy is received; and
   a processor housed in the handle and configured to generate a composite image from the image formed for each wavelength of illumination energy based on the sequence.

8. The apparatus of claim 7, wherein the image capture device is configured to form at least a first image for the first wavelength of the first illumination energy and a second image for the second wavelength of the second illumination energy.

9. The apparatus of claim 8, wherein the illumination energy emitted by the at least one illumination light source includes a third illumination energy of a third wavelength different from the first wavelength and the second wavelength, the illumination control system is further configured to control the illumination energy to output the third illumination energy in the sequence, the image capture device is configured to form a third image for the third wavelength of the third illumination energy, and the first, second, and third wavelength of the first, second, and third illumination energy correspond to a green, a blue, and a red light, respectively.

10. The apparatus of claim 7, wherein the processor is further configured:
    receive and process a plurality of images formed by the image capture device to determine a timing of the formation of the plurality of images; and
    cause the illumination control system to output each illumination energy in the sequence, including the first illumination energy and the second illumination energy, at a timing and for a duration that is synchronized to the determined timing of the formation of the plurality of images such that the image capture device is enabled to form the image for each wavelength of illumination energy one at a time as the one wavelength is output at the given time in the sequence.

11. An apparatus comprising:
    a member having a proximal end including a handle and a distal end configured to be at least partially inserted into a patient;
    at least one illumination light source configured to emit at least a first illumination energy at a first wavelength and a second illumination energy at a second wavelength different than the first wavelength onto an object;
    an illumination control system connected to the at least one illumination light source and housed in the handle, wherein the illumination control system is configured to control an output sequence of the first illumination energy and the second illumination energy such that only one wavelength of the different wavelengths is output at a given time in the sequence;
    an image capture device including a plurality of pixels disposed at the distal end of the member and configured to detect illumination energy of each wavelength in the visible spectrum and only one wavelength in the visible spectrum at a given time, wherein, based on the sequence, the image capture device is configured to form an image for each wavelength of illumination energy that is emitted from the at least one illumination light source, reflected off of the object onto which the illumination energy is emitted, and detected by each of the plurality of pixels, including at least a first image for the first wavelength of the first illumination energy detected by each of the plurality of pixels when the first illumination energy is emitted and a second image for the second wavelength of the second illumination energy detected by each of the plurality of pixels when the second illumination energy is emitted; and a processor housed in the handle and configured to generate a composite image from the image formed for each wavelength of illumination energy based on the sequence.

12. The apparatus of claim 11, wherein the processor is configured to cause the illumination control system to output illumination energy corresponding to each wavelength of illumination energy, including the first illumination energy and the second illumination energy, at a particular timing and for a particular duration in the sequence.

13. The apparatus of claim 11, wherein the composite image is formed based on an intensity of the illumination energy of each wavelength.

14. The apparatus of claim 11, wherein the at least one illumination light source includes a plurality of pump light sources, and the apparatus further comprises:

a plurality of optical fibers connected to the plurality of pump light sources and disposed within the member, each optical fiber being configured to transmit a different illumination energy in the sequence controlled by the illumination control system to output the different wavelengths from the optical fiber toward the object.

* * * * *